United States Patent
Birkenbach (10) Patent No.: US 11,992,284 B2
(45) Date of Patent: May 28, 2024

(54) IMAGE BASED MOTION CONTROL CORRECTION

(71) Applicant: Brainlab AG, Munich (DE)

(72) Inventor: Rainer Birkenbach, Munich (DE)

(73) Assignee: Brainlab AG, Munich (DE)

( * ) Notice: Subject to any disclaimer, the term of this patent is extended or adjusted under 35 U.S.C. 154(b) by 210 days.

(21) Appl. No.: 17/629,489

(22) PCT Filed: Aug. 30, 2019

(86) PCT No.: PCT/EP2019/073245
§ 371 (c)(1),
(2) Date: Jan. 24, 2022

(87) PCT Pub. No.: WO2021/037381
PCT Pub. Date: Mar. 4, 2021

(65) Prior Publication Data
US 2022/0408002 A1    Dec. 22, 2022

(51) Int. Cl.
| | | |
|---|---|---|
| *A61B 34/37* | (2016.01) | |
| *A61B 1/00* | (2006.01) | |
| *G16H 40/63* | (2018.01) | |
| *H04N 23/50* | (2023.01) | |
| *H04N 23/62* | (2023.01) | |
| *H04N 23/68* | (2023.01) | |

(52) U.S. Cl.
CPC .......... *A61B 34/37* (2016.02); *A61B 1/00009* (2013.01); *G16H 40/63* (2018.01); *H04N 23/62* (2023.01); *H04N 23/6811* (2023.01); *H04N 23/685* (2023.01); *H04N 23/555* (2023.01)

(58) Field of Classification Search
CPC .. H04N 23/62; H04N 23/6811; H04N 23/685; H04N 23/555; G06T 7/80; A61B 34/37; A61B 1/00009; A61B 1/0016
See application file for complete search history.

(56) References Cited

U.S. PATENT DOCUMENTS

| | | | |
|---|---|---|---|
| 2016/0374541 A1 | 12/2016 | Agrawal et al. | |
| 2017/0143442 A1* | 5/2017 | Tesar | H04N 23/63 |
| 2018/0177556 A1 | 6/2018 | Noonan | |
| 2019/0075230 A1* | 3/2019 | Takeda | H04N 23/631 |
| 2021/0011272 A1* | 1/2021 | Ko | G06T 1/0007 |

FOREIGN PATENT DOCUMENTS

| | | |
|---|---|---|
| EP | 1172183 A2 | 1/2002 |
| EP | 2026589 A1 | 2/2009 |
| WO | 2018/064394 A1 | 4/2018 |

OTHER PUBLICATIONS

Li, et al. Simultaneous Robot-World and Hand-Eye Calibration Without a Calibration Object, dated Nov. 15, 2018, 16 pages.

* cited by examiner

*Primary Examiner* — Kelly L Jerabek
(74) *Attorney, Agent, or Firm* — Tucker Ellis LLP (57) ABSTRACT

The present invention relates to a method of adjusting control commands for moving a medical camera connected to a motorized support structure, wherein the adjustment is based on images provided by the camera. Based on a comparison of at least two images provided by the camera, an actual motion of the camera is determined and compared with an intended motion defined by a control command forwarded to the motorized support structure. In case a deviation between the intended motion and the actual motion is determined, a correction is applied to the control command such that the actual motion of the camera coincides with the intended motion.

13 Claims, 3 Drawing Sheets

IMAGE BASED MOTION CONTROL CORRECTION

RELATED APPLICATION DATA

This application is a National Phase application of International Application No. PCT/EP2019/073245, filed Aug. 30, 2019, the contents of which are incorporated herein by reference.

FIELD OF THE INVENTION

The present invention relates to a computer-implemented method for adjusting/correcting control commands for moving a medical imaging device connected to a moving device, a corresponding computer program, a program storage medium storing such a program and a computer for executing the program, as well as a medical system comprising an electronic data storage device and the aforementioned computer.

TECHNICAL BACKGROUND

Diagnostic medical procedures often involve the use of cameras to visualize anatomical structures which are difficult or even impossible to see with the naked eye. In such cases, cameras help in visualizing those anatomical structures by being placed in the vicinity of those structures with an unobstructed line of sight and by transmitting the received images to a remote display or monitor that can be easily observed by a medical practitioner. For example, endoscopic procedures utilize cameras to examine and visualize the interior of hollow organs or cavities within a patient's body. Common endoscopes have an elongated instrument body with a distal section that is usually placed within the patient's body, and a proximal section that usually remains outside the patient's body. While the distal endoscope section is provided with the at least one camera, the entire endoscope body can be held in place by a support structure which connects to the proximal section of the endoscope and which may be motorized, such that a medical practitioner can move the endoscope together with the camera to a desired location by controlling the motorized support structure via a user interface. Since common endoscopes have a tube-shaped and rotationally symmetrical endoscope body, it is possible and in many cases also desired that the endoscope along with the camera can be attached to the support structure in various orientations around its longitudinal axis, wherein the endoscope often keeps a rotational degree of freedom around its longitudinal axis even when it is held by the support structure.

In order to provide, acquire and process digital data relying on spatial directions, each one of the medical appliances involved in such robotic endoscopy has a predefined coordinate system assigned. The remaining rotational degree of freedom of the endoscope camera with respect to a motorized support structure holding the endoscope and the camera in place therefore often leads to a situation in which a user wants the camera image displayed on a monitor to move into a certain direction and intuitively manipulates an input device, for example a joystick, but receives an unexpected response as the displayed image moves into another direction than intended by the user.

In the past, medical practitioners encountered this problem either by initially rotating the endoscope within the support structure until the control command directions coincide with the directions the endoscope and the displayed images are actually moved in, or by simply mentally adapting to the non-conformance between the intended and the actually provoked moving directions of the image displayed on the screen. However, neither of those approaches is user-friendly nor suitable to new and unexperienced personnel.

Prior art approaches to correct for this control-reaction-deviation, that allow for more intuitive and therefore user-friendly use of robotic endoscopes provide an automatic image correction which is based on sensor data. For example, the endoscope may be provided with a gyro-sensor via which recognizes by which angle the endoscope is rotated with respect to the support structure, such that the displayed endoscope image can be computationally corrected by rotating it by the same amount. Those automatic image corrections however come along with a certain loss in image quality and a certain time-lag between the control inputs and the corresponding motions of the displayed image.

The present invention has the object of overcoming the deficiencies of the prior art approaches by providing an intuitive, user-friendly but yet uncomplicated approach of controlling a robotic endoscope.

The present invention can be used for any procedures that involve the use of at least one camera being supported by a motorized structure which is controlled by manual user inputs.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present invention relates to a method of adjusting control commands for moving a medical camera connected to a motorized support structure, wherein the adjustment is based on images provided by the camera. Based on a comparison of at least two images provided by the camera, an actual motion of the camera is determined and compared with an intended motion defined by a control command forwarded to the motorized support structure. In case a deviation between the intended motion and the actual motion is determined, a correction is applied to the control command such that the actual motion of the camera coincides with the intended motion.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of adjusting control commands for moving a medical imaging device which is connected to a moving device. The method comprises executing, on at least one processor of at least one computer (for example at least one computer being part of a navigation system), the following exemplary steps which are executed by the at least one processor.

In a (for example first) exemplary step, first image data is acquired, describing a first image received by the medical imaging device.

In a (for example second) exemplary step, intended motion data is acquired, describing an intended motion of the medical imaging device, wherein the intended motion data is based on a control command transmitted to the moving device.

In a (for example third) exemplary step, second image data is acquired, describing a second image received by the medical imaging device that has been moved as a result of the control command.

In a (for example fourth) exemplary step, actual motion data is determined based on the first image data and the second image data, describing an actual motion of the medical imaging device.

In a (for example fifth) exemplary step, correction data is determined based on the intended motion data and the actual motion data, describing a correction to be applied to the control command in order to produce the intended motion of the medical imaging device.

In other words, the inventive approach of adjusting or correcting control commands includes the acquisition of at least two images via a camera prior and subsequent to a camera motion initiated by an input command. A comparison of the image content allows determining the motion the camera has actually performed. For example, an overall motion vector can be calculated on the basis of a positional difference of at least one, preferably of a plurality of features in the at least two images obtained. In a specific case, when all or almost all recognizable features have moved between two obtained images by the same amount and in the same direction, i.e. described by the same motion vector within the displayed image plane, it can be assumed that the camera has been moved translatory and substantially perpendicularly to the camera's line of sight. If, in another case, the camera has been rotated about its line of sight, the recognizable features seen in both obtained images will describe a vector-field around a center point that represents the camera's center of rotation within the image plane. If, in still another exemplary case, the image features as seen in the obtained images describe a vector-field with the specific vectors converging to or diverging from a specific center point, it can be assumed that the camera is moved towards or away from an observed object along the camera's line of sight. Of course, an actual motion of the camera during a medical procedure can be superimposed by any conceivable combination of the above described exemplary motions.

In summary, the present invention makes use of at least two images obtained by the camera to determine a motion the camera has actually performed between the compared images.

In accordance with the present invention this actual motion determined via an image comparison is then compared with an intended motion of the camera, which is represented by a control command addressed to the motorized support structure of the camera. For example, the intended motion can be compared with the actual motion by comparing the respective overall motion vectors calculated from the control command and the obtained images, respectively.

In case the compared motions, or to be more specific, the compared overall motion vectors show a deviation between the intended motion and the actual motion, it is the object of the present invention to determine a correction which is then applied to the control command such that the actual camera motion coincides with the intended motion, for example for future control commands or even the current control command for which the actual motion initially deviated.

In order to compare the respective motions/motion vectors with each other, it is conceivable that the respective motions/motion vectors are correlated to each other within a common coordinate system. For example, such common coordinate system can be assigned to the display device on which the camera images are shown to the practitioner during endoscopy. For example, the spatial directions such as "up", "down", "left", "right" for the actual motion and the intended motion may be defined as the directions "up", "down", "left" and "right" on the display screen. Consequently, the directions "in" and "out" may be defined as being perpendicular to the screen plane directed towards and away from the screen, respectively. Of course, the common coordinate system could be assigned to any other technical appliances apart from the monitor that displays the camera images.

In a practical example, a medical practitioner who is performing an endoscopic procedure with the present invention may wish the camera image which is currently shown on the display to move "downwards" with respect to the monitor. The control command for initiating such motion may be defined as an "up" (or "down"-)-control which is input by the user via a user interface such as a joystick, computer mouse or touch-sensitive touchpad. After performing the corresponding "up"- (or "down"-) command by pushing the joystick or computer mouse, or a finger across the touchpad forwards (or downwards), a corresponding control signal is transmitted to the motorized support structure which accordingly performs a predefined motion along with the camera.

Since the coordinate systems assigned to the devices a practitioner directly interacts with (e.g. an input device such as a joystick and a display device such as a monitor) is, for reasons explained further above, not fixedly corrected with respect to the coordinate systems assigned to devices (e.g. a motion device such as a motorized camera support structure, and an imaging device such as a camera) which directly affect the actual motion of the images, the present invention provides an "on the fly" correction such that the practitioner receives an image motion which he or she intuitively expects as a result from the control input.

While the control command can be manually effected by a practitioner via an input device such as a digital or analogue joystick, a computer mouse, a touchpad or any other suitable input device, a control command may be also automatically generated and transmitted by a control device. For example, such control device may be programmed to transmit a specific control command to the motorized support structure in order to have the system corrected. For example, such automatic control commands can be issued at predefined time intervals and/or for predefined conditions. For example, an automatic control command could be issued at the beginning of an endoscopic procedure such that the system is corrected once before the camera is used for endoscopy. However, such correction procedure may be also performed every time the user activates the input device for performing an input command. In such case, it is the automatically issued control command which is used for correcting the system, such that a subsequent manual control command already results in an expected response, i.e. an expected motion of the image displayed on the screen.

While the intended motion may include an intended direction of motion of the medical imaging device, it may also include an intended velocity of motion of the medical imaging device. The intended velocity of motion can be a function of a dimension of the display device, particularly of at least one of the width, the height, the size and the pixel numbers of the display device, such that a user always experiences the same or roughly the same speed a camera image moves over the screen, irrespective of the specific properties of the monitor or display. In other words, the system may not only be corrected in terms of the directions the camera can be moved in, but also the speed the camera is moved. For example, a practitioner deflecting an analogue joystick by a relatively small angle will expect the camera to move rather slowly. However, if the camera is placed very near an object to be observed, even a rather slight deflection of the joystick may result in a camera image rushing over the screen. On the other hand, if the camera is placed comparatively far from the object to be observed, even a large deflection of the joystick may only result in a hardly noticeable motion of the camera image on the screen. This is because a system for which the motors of the motorized camera support structure are fixedly corrected to a certain control command amplitude (e.g. joystick deflection) does not take into account the distance between the camera and the object to be observed by the camera. This may lead to the aforementioned undesired situations which are rather uncomfortable for a user. In order to encounter this problem, the present invention can provide measures to control the velocity the camera is moved as a function of the velocity the image content moves across the display screen. Thus, a user receives a definite speed of the image on the screen as a response to a definite amplitude of an input command, irrespective of how far the camera is placed from the observed object. In this context, an input via a digital joystick may evoke a predefined speed of the image on the screen, irrespective of the distance between the camera and the observed object. In terms of the inventive method, this means that the correction applied to the control command depends on the distance the image content moves across the screen between the first and the second image.

Further, the inventive method may only consider directions of motion which are parallel to the plane of the images received by the camera. In other words, the present invention may only consider 2D-controls. However, the present invention may also consider directions of motion which are perpendicular to the image plane, i.e. "in"- and "out"- directions with respect to the image plane. While it is conceivable that such "zoom in"- and "zoom out"-control commands are input via the same input devices than the previously described 2D-control commands, for example via a scroll-wheel of a computer mouse, any of the 3D-control commands can be input via separate input devices dedicated to one or more dimension(s) or direction(s), for example via separate joysticks and/or levers.

In order to determine the direction and/or the velocity of motion of the video image across the screen, i.e. of the motion of image features or objects between the first image and the second image, any conceivable image processing techniques known in the art can be applied. For example, the "optical flow" of the displayed image content can be determined as well as the "ego motion" of the camera with respect to the environment observed by the camera. Further, any techniques based on edge- and/or feature-detection as well as any techniques based on image-comparison may be used in the context of the present invention.

In case the correction procedure is performed on the basis of a control command which is input by a practitioner to move the camera, the correction applied to the control command may further compensate for the difference between an actual position and an intended position of the medical imaging device, that was caused by a deviation of the actual motion from the intended motion of the medical imaging device. In other words, the "uncorrected" camera motion which occurred between the first and the second image, and which was needed for the correction procedure, results in an unintended motion of the camera and therefore in an unintended position of the camera. This incorrect camera position may be compensated for by an additional, opposed camera motion such that the overall actual camera motion exactly complies with the intended camera motion— as if there had never been an uncorrected and therefore "false" motion. For example, such compensation could be applied right after the correction has been applied to the control command, such that the camera is immediately brought "back on track" before the remaining control command is followed by the camera exactly as intended by the user. Further, the compensation may be also applied at any later point in time, for example at the end of the control command, such that the camera is brought back on track after having moved parallel to the intended track.

As already referred to further above, the correction data can be determined for every control command transmitted to the moving device, such that a new correction is applied to every control command.

Moreover, in order to save the user from any confusion that may be caused by an initially uncorrected and therefore false camera motion, the display device may be controlled not to show in the sequence of images a motion of the medical imaging device that deviates from the intended motion. In other words, the display device may either show a black screen or static (camera) image for the time period the correction procedure is performed, which is expected to be a rather short and therefore unnoticeable time period, the major part of which is taken up by the time period between the acquisitions of the first image and the second image, respectively.

In a further embodiment of the present invention, determining correction data involves applying a plausibility check to determine whether the determined correction of the control command is reasonable, particularly wherein a reasonable correction of the control command does not exceed a maximum limit and/or a minimum limit. For example, if it is determined within a 2D-control environment, that a control command which is meant to move the camera within the image plane results in a motion of the camera perpendicularly to the image plane, a plausible correction cannot be applied to the control command within the limits of the 2D-environment. Such cases should be brought to the user's attention, for example by generating a visual, haptic or acoustic feedback to the user, for example via a vibrating joystick or an error message shown on the monitor.

In a further exemplary embodiment of the present invention, the method further includes the step of determining correction verification data, describing whether the control command has been validly corrected, particularly based on at least a third image received by the medical imaging device that has been moved as a result of the corrected control command. For example, a third image may be acquired after the camera has been moved in accordance with a corrected control command. In case the control command has been properly corrected, the actual motion performed between the second and the third image should not deviate from the intended motion, or should at least not exceed a predefined tolerance threshold. If this is however the case, further correction data may be determined based on the intended motion and the actual motion between the second and the third image, such that a subsequent correction can be applied to the control command in order to produce the intended motion of the medical imaging device between the second and the third image. In other words, the inventive method may be performed iteratively until the actual camera motion corresponds to the intended camera motion. However, it may for some cases be reasonable to issue an error message in case the control command cannot be corrected within a predefined number of correction loops, e.g. within three correction-loops, since this may indicate an error in the system's setup.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission.

The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
 a) the at least one computer according to the fourth aspect; and
 b) a moving device for moving a medical imaging device connected to the moving device;
  wherein the at least one computer is operably coupled to
 a) the moving device for issuing a control signal to the moving device for controlling the operation of the moving device on the basis of the first and the second image data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

The present invention also relates to the use of the device/system or any embodiment thereof for adjusting the above described control commands.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
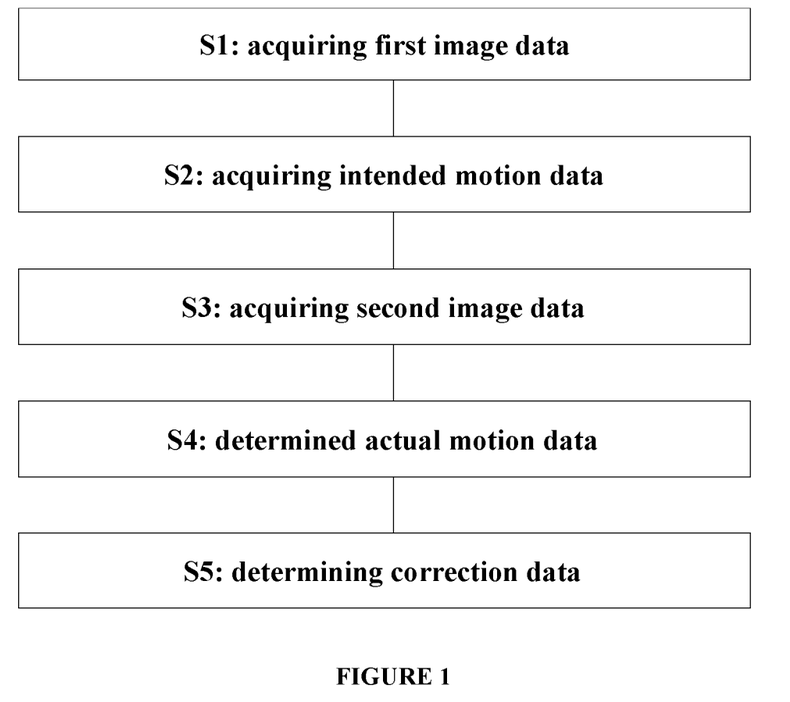
FIG. 1 illustrates the basic steps of the control adjustment method in accordance with the present invention.

FIG. 1 shows the basic steps of the inventive control adjustment method in accordance with the present invention. In a first step S1, first image data is acquired via at least one (endoscope) camera, whereupon, in second step S2, intended motion data is acquired from an input device. In this respect it should be noted that the steps of acquiring first image data and acquiring intended motion data may be also performed in a reverse order. In a third step S3, second image data is acquired via the (endoscope) camera, such that, in a fourth step S4, actual motion data can be determined from the first image data and the second image data. In a fifth step S5, the determined actual motion data is compared with the acquired intended motion data so as to determine correction data that describes a correction to be applied to the control command, such that the actual camera motion corresponds to the intended camera motion.

Figure 2:
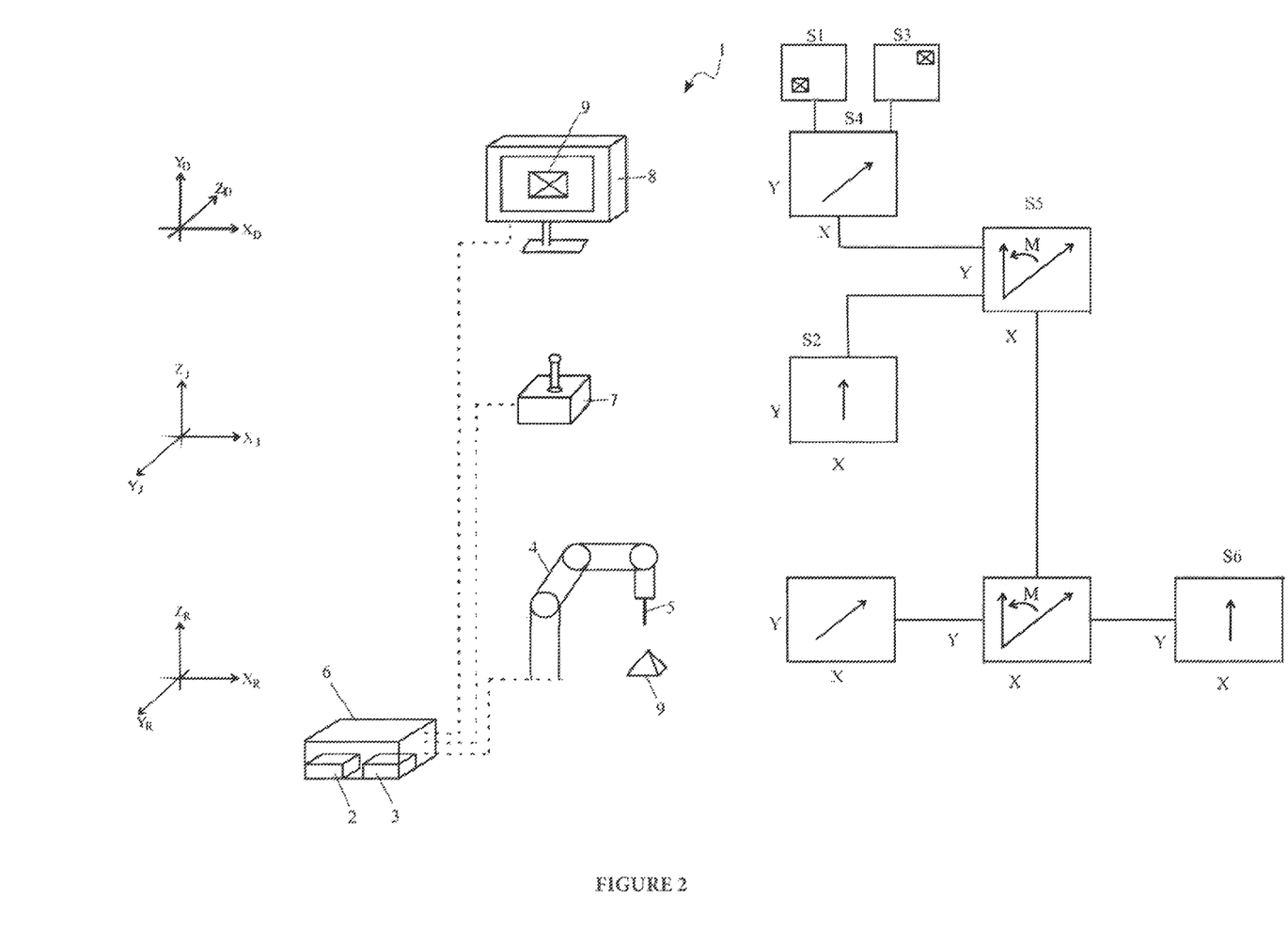
FIG. 2 shows a schematic system setup in accordance with the present invention along with a schematic illustration of a control command correction in accordance with the present invention.
Figure 3:
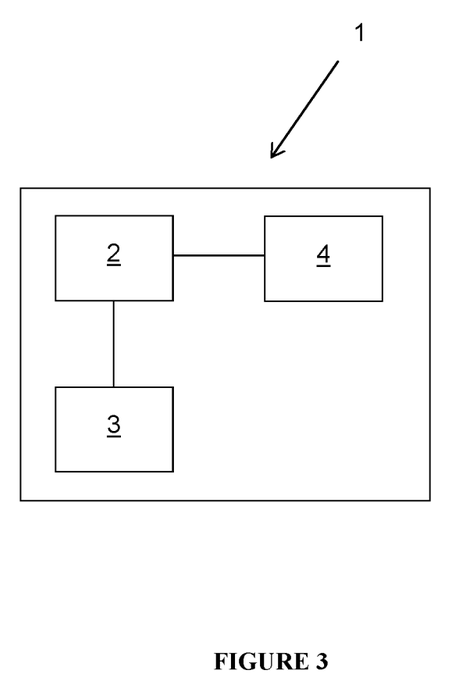
FIG. 3 shows a schematic illustration of the system according to the fifth aspect.

FIGS. 2 and 3 shows the basic components of a system setup in accordance with the present invention. A medical endoscopy system 1 comprises a monitor 8, a joystick 7 and a semi-robotic support arm 4 comprising a plurality of arm-sections which are connected to each other via motorized joints such that the arm-sections can be moved with respect to each other. At the distal end of the motorized support arm 4 an endoscopic camera 5 is held in place above a structure 9 (represented by a pyramid) to be observed via the endoscope camera 5, with the camera's line of sight being directed towards the structure 9.

Further, the system 1 comprises a control device 6 for performing the inventive control adjustment method, which is connected to the motorized support structure 4, the endoscopic camera 5, the joystick 7 and the monitor 8. The control device includes a computer 2 having a digital processor for performing the inventive control adjustment method, and a program storage medium 3 with a program that causes the computer to perform the method steps of the inventive method.

In a first step S1, the camera 5 acquires an image of the structure 9, wherein the image data is transferred via the control device to the monitor 8 which then shows an image of the structure 9. As can be seen in the frame of FIG. 2, which corresponds to step S1, the structure 9 is shown on the monitor in the bottom left corner of the displayed image.

A user who may not wish the structure 9 to be displayed on the bottom left corner of the display 8 may input a control command via the joystick 7 to cause the motorized support structure 4 to move the endoscope camera 5 with respect to the structure 9, such that structure 9 is then shown at the top left corner of the image shown by the monitor 8. In order to do so, the user may push the joystick in an "up"-direction as this is schematically shown in the frame which corresponds to step S2. After the control command which represents the intended motion of the camera 5 has been input and the motorized support structure 4 has accordingly moved, it may occur that the structure 9 is not shown as intended at the top left corner of the image, but instead at the top right corner of the image (cf. the frame which corresponds to step S3). By performing image processing techniques in order to compare the camera images acquired in steps S1 and S3, an actual motion of the support structure 4 is calculated in step S4 and it is found that the structure 9 has not moved in an "up"-direction in the image, but rather in an "up"-direction and a "right"-direction. Consequently, the actual camera motion (cf. frame corresponding to step S4) deviates from an intended camera motion (cf. frame corresponding to step S2). For example, this deviation may be the result of a rotational degree of freedom of the endoscope camera 5 along its line of sight and with respect to the support arm 4. In any case, the deviation of the actual camera motion from the intended camera motion is undesired as it causes confusion for the practitioner operating the endoscope camera 5 via the joystick 7 and the monitor 8.

In order to compensate for this unwanted deviation, the present invention determines a correction to be applied to the control command such that it produces the intended motion of the camera 5. As schematically shown in the frame according to method step S5, a transformation matrix M is calculated which transforms the vector which represents the actual motion to the vector which represents the intended motion. This calculated correction matrix M may then be applied to any control command which is transmitted to the support arm 5 subsequent to the second image, such that the camera 5 moves as intended and in accordance with the control commands input via the joystick 7 (cf. frame according to method step S6).

In case the correction matrix M is not valid anymore, for example if the camera 5 rotates with respect to the support arm 4 after the correction matrix M has been calculated, a further control correction can be performed in the same manner as previously described in order to calculate a new, updated correction matrix M.

The invention claimed is:

1. A computer-implemented method of adjusting control commands for moving an associated imaging device coupled with an associated moving device that is operable to move the associated imaging device, the method comprising:

acquiring first image data that describes a first image of an associated structure received by the associated imaging device;

acquiring intended motion data that describes an intended motion of the associated imaging device, wherein the intended motion data is based on a control command received by the associated moving device;

acquiring second image data that describes a second image of the associated structure received by the associated imaging device that has been moved by the associated moving device as a result of the associated moving device receiving the control command;

determining actual motion data based on the first image data and the second image data, wherein the actual motion data describes an actual motion of the associated imaging device;

determining correction data based on the intended motion data and the actual motion data, wherein the correction data describes a correction to be applied to the control command to:
  produce the intended motion of the associated imaging device; and
  compensate for a difference between an actual position of the associated imaging device and an intended position of the associated imaging device that was caused by a deviation between the actual motion of the associated imaging device and the intended motion of the associated imaging device; and determining, based on the correction data, control data describing a corrected control command to be transmitted to the associated moving device.

2. The method according to claim 1, wherein the determining the correction data comprises correlating the intended motion data with the actual motion data in a coordinate system that is common to both the intended motion data and the actual motion data, the coordinate system comprising a coordinate system of an associated display device that is adapted to display images that are received by the associated imaging device.

3. The method according to claim 1, wherein the acquiring the intended motion data comprises acquiring intended motion data that is based on a control command that is effected by at least one of:
  a user control command input transmitted by an associated input device; and/or
  an automatic control command generated and transmitted by an associated control device.

4. The method according to claim 1, wherein the acquiring the intended motion data comprises acquiring intended motion data that describes:
  an intended direction of motion of the associated imaging device; and/or
  an intended velocity of motion of the associated imaging device.

5. The method according to claim 4, wherein the acquiring the intended motion data that describes the intended direction of motion of the associated imaging device comprises:
  acquiring intended motion data that describes an intended direction of motion of the associated imaging device that is parallel to a plane of at least one of the first image and/or the second image.

6. The method according to claim 4, wherein the acquiring the intended motion data that describes the intended velocity of motion of the associated imaging device comprises:
  acquiring intended motion data that describes an intended velocity of motion of the associated imaging device that comprising a function of a dimension of an associated display device comprising at least one of:
    a width of the associated display device;
    a height of the associated display device;
    a size of the associated display device; and/or
    a pixel number of the associated display device.

7. The method according to claim 1, wherein the determining the actual motion data comprises determining the actual motion data by image processing determining the motion of the associated imaging device relative to the associated structure displayed on an associated display device with a first image corresponding to the first image data and a second image corresponding to the second image data.

8. The method according to claim 1 wherein the determining the correction data comprises determining the correction data for every control command received by the associated moving device.

9. The method according to claim 1 further comprising controlling an associated display device to not show in a sequence of images a motion of the associated imaging device that deviates from the intended motion.

10. The method according to claim 1, wherein the determining the correction data comprises applying a plausibility check to determine whether the determined correction of the control command is reasonable, particularly wherein a reasonable correction of the control command does not exceed a maximum limit and/or a minimum limit.

11. The method according to claim 1, further comprising determining correction verification data, describing whether the control command has been validly corrected, particularly based on at least a third image received by the associated imaging device that has been moved as a result of the corrected control command.

12. A program logic stored in a memory device of a computer that when executed on the computer or when loaded onto the computer, causes the computer to perform a method of adjusting control commands for moving an associated imaging device coupled with an associated moving device that is operable to move the associated imaging device, the method comprising:
  acquiring first image data that describes a first image of an associated structure received by the associated imaging device;
  acquiring intended motion data that describes an intended motion of the associated imaging device, wherein the intended motion data is based on a control command received by the associated moving device;
  acquiring second image data that describes a second image of the associated structure received by the associated imaging device that has been moved by the associated moving device as a result of the associated moving device receiving the control command;
  determining actual motion data based on the first image data and the second image data, wherein the actual motion data describes an actual motion of the associated imaging device;
  determining correction data based on the intended motion data and the actual motion data, wherein the correction data describes a correction to be applied to the control command to:
    produce the intended motion of the associated imaging device; and
    compensate for a difference between an actual position of the associated imaging device and an intended position of the associated imaging device that was caused by a deviation between the actual motion of the associated imaging device and the intended motion of the associated imaging device; and determining, based on the correction data, control data describing a corrected control command to be transmitted to the associated moving device.

13. A system comprising:

a computer comprising a processor and a memory device, wherein the computer is operable to execute program logic stored in the memory device to perform a method of adjusting control commands for moving an imaging device coupled with a moving device that is operable to move the imaging device, the method comprising:

acquiring first image data that describes a first image of an associated structure received by the imaging device;

acquiring intended motion data that describes an intended motion of the imaging device, wherein the intended motion data is based on a control command received by the moving device;

acquiring second image data that describes a second image of the structure received by the imaging device that has been moved by the moving device as a result of the moving device receiving the control command;

determining actual motion data based on the first image data and the second image data, wherein the actual motion data describes an actual motion of the imaging device; and determining correction data based on the intended motion data and the actual motion data, wherein the correction data describes a correction to be applied to the control command to:

produce the intended motion of the imaging device; and compensate for a difference between an actual position of the associated imaging device and an intended position of the associated imaging device that was caused by a deviation between the actual motion of the associated imaging device and the intended motion of the associated imaging device;

determining, based on the correction data, control data describing a corrected control command to be transmitted to the associated moving device; and a moving device operable to move a imaging device connected with the moving device, wherein the computer is operably coupled to the moving device for issuing a control signal to the moving device for controlling the operation of the moving device based on the corrected control command.

* * * * *